(12) United States Patent
Sailer et al.

(10) Patent No.: US 7,041,645 B2
(45) Date of Patent: May 9, 2006

(54) METHODS OF INHIBITING OR INDUCING BONE FORMATION

(75) Inventors: Hermann Sailer, Zurich (CH); Franz Weber, Singen (DE)

(73) Assignee: The University of Zurich, Zurich (CH)

( * ) Notice: Subject to any disclaimer, the term of this patent is extended or adjusted under 35 U.S.C. 154(b) by 0 days.

(21) Appl. No.: 10/189,302

(22) Filed: Jul. 2, 2002

(65) Prior Publication Data

US 2003/0045474 A1   Mar. 6, 2003

(30) Foreign Application Priority Data

Jul. 5, 2001   (FI)   ................................. 20011478

(51) Int. Cl.
   *A61K 38/16*   (2006.01)
   *A61K 38/17*   (2006.01)
   *A61K 38/18*   (2006.01)
   *A61K 38/19*   (2006.01)
(52) U.S. Cl. ................. 514/12; 514/2; 514/8; 424/85.1
(58) Field of Classification Search .................... 514/2; 424/85.1
   See application file for complete search history.

(56) References Cited

U.S. PATENT DOCUMENTS

| | | | |
|---|---|---|---|
| 4,563,489 A | 1/1986 | Urist | 524/21 |
| 5,399,677 A | 3/1995 | Wolfman et al. | 536/23.5 |
| 5,631,142 A | 5/1997 | Wang et al. | 435/69.1 |
| 5,854,207 A * | 12/1998 | Lee et al. | 514/2 |
| 6,180,606 B1 | 1/2001 | Chen et al. | 514/12 |
| 6,245,889 B1 | 6/2001 | Wang et al. | 530/350 |

FOREIGN PATENT DOCUMENTS

| | | |
|---|---|---|
| FI | 103278 | 5/1999 |
| WO | WO 92/09697 | 6/1992 |
| WO | WO 93/09229 | 5/1993 |
| WO | WO 00/56879 | 9/2000 |
| WO | WO 00/64460 | 11/2000 |

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Vukicevic et al., 1996, PNAS USA 93:9021-9026.*
Massague, 1987, Cell 49:437-438.*
Pilbeam et al., 1993, Bone 14:717-720.*
Isobe et al., "Bone morphogenetic protein encapsulated with a biodegradable and biocompatible polymer," *J. Biomed. Mat. Res.*, 32:433-438 (1996).
Weber et al., "Disulfide Bridge Conformers of Mature BMP Are Inhibitors for Hetertopic Ossification," *Biochem. and Biophys. Res. Comm.*, 286:554-558 (2001).
Wozney and Rosen, "Bone Morphogenetic Protein and Bone Morphogenetic Protein Gene Family in Bone Formation and Repair," *Clin. Ortho. and Rel. Res.*, 346:26-37 (1998).
DiCesare et al., "Effects of indomethacin on demineralized bone-induced heterotopic ossification in the rat," *J. Orthop. Res.*, 9:855-861 (1991).
Muthukumaran and Reddi, "Dose-dependence of the threshold for optimal bone induction by collagenous bone matrix and osteogenin-enriched fraction," *Collagen Rel. Res.*, 8:433-441 (1988).
O'Connor, "Animal models of heterotopic ossification," *Clin. Orthop.* 346:71-80 (1998).
Wozney "Bone Morphogenetic Proteins," *Progress in Growth Factor Research*, 1:267-280 (1989).

* cited by examiner

*Primary Examiner*—Elizabeth Kemmerer
(74) *Attorney, Agent, or Firm*—Banner & Witcoff, Ltd.

(57) ABSTRACT

The present invention relates to a pharmaceutical composition containing a mixture of stable folding variants of recombinant bone morphogenic proteins (rBMPs) and its use in therapy, especially in the treatment of orthopaedic and dental patients. Specifically, the present invention relates to a pharmaceutical composition containing a mixture of stable folding variants of at least two rBMPs or their monomers or mutants in a suitable carrier system.

13 Claims, 5 Drawing Sheets

METHODS OF INHIBITING OR INDUCING BONE FORMATION

This application claims the benefit of the filing date of Finnish Patent Application No. 20011478, filed on Jul. 5, 2001.

FIELD OF THE INVENTION

The present invention relates to a pharmaceutical composition containing a mixture of stable folding variants of recombinant bone morphogenic proteins (rBMPs) and to its use in therapy, especially in the treatment of orthopaedic and dental patients. Specifically, the present invention relates to a pharmaceutical composition containing a mixture of stable folding variants of at least two rBMPs or their monomers or mutants in a suitable carrier system.

BACKGROUND OF THE INVENTION

Urist published first studies on bone formation by autoinduction and disclosed new protein factors involved in therein in 1965 [Urist, M. R., Science 150 (1965) 447–454]. The bone inducing principle could not be attributed to a single protein, but to a group of proteins, where each group member alone is sufficient to induce heterotopic ossification (HO). This started a long search for the bone inducing principle, and it took over twenty years before the first cDNAs encoding bone morphogenetic proteins or BMPs were cloned [Wozney, J. M., et al., Science 242 (1988) 1528–1534]. Based on sequence and structural analysis, additional proteins like the growth and differentiation factors (GDFs) could be linked to the original BMPs. Together they build the BMP-family with more than thirty members [Reddi, H., Cytokine & Growth Factor Reviews 8 (1997) 11–20], which belongs to the TGF-β-super-family.

The BMP-family is divided to subfamilies including the BMPs, such as BMP-2 and BMP-4, osteogenic proteins (OPs), such as OP-1 or BMP-7, OP-2 or BMP-8, BMP-5, BMP-6 or Vgr-1, cartilage-derived morphogenetic proteins (CDMPs), such as CDMP-1 or BMP-14 or GDF-5, growth/differentiation factors (GDFs), such as GDF-1, GDF-3, GDF-8, GDF-9, GDF-11 or BMP-11, GDF-12 and GDF-14, and other subfamilies, such as BMP-3 or osteogenin, BMP-9 or GDF-2, and BMP10 (Reddi et al., supra).

One common feature shared by the BMP-family members and other members of the TGF-β super-family is the overall folding topology which resembles a hand exhibiting the victory sign, with the wrist representing the central alpha-helix, two fingers representing two anti-parallel β-sheets, and the palm representing the cysteine-knot region [Scheufeler, C. et al., J. Mol. Biol. 287 (1999) 103–115]. The cysteine-knot consists of three intrachain disulfide bridges and is the main stabilizer of the 3-D structure, and it is so effective that biological activity is preserved even after extensive exposure to low pH, urea or guanidine hydrochloride treatments [Sampath, T. K., and Reddi, A. H., Proc. Natl. Acad. Sci. USA 78 (1981) 7599–7603]. Further stabilization of the topology is achieved by the dimerization of two monomers, creating an internal hydrophobic core (Scheufeler, C. et al., supra). The overall dimeric structure is also necessary for the biological action, such as osteoinduction, as it enables the simultaneous binding of a dimeric molecule to the corresponding receptor, for instance the simultaneous binding of a BMP-dimer to a type I and a type II serine/threonine receptor forming a heterotetramer, triggering a signal cascade via the phosphorylation of Smads [Yamashita, H. and Miyazono, K., Nippon Rinsho 57 (1999) 220–226].

Results based on the protein and nucleotide sequences of the BMPs have revealed that the morphogenesis of bone, comprising chemotaxis, mitosis, and differentiation, is governed by the action of the BMPs. It has also been shown that the effects of the BMPs are not limited to bone and cartilage. In the early stage of embryogenesis the BMPs rule the formation of the entire body plan and specify the tissue types and axes. In an adult, the BMPs affect to the ability of bones to repair successfully [for review, see Wozney, J. and Rosen, V., Clin. Orthop. Rel. Res. 346 (1998) 26–37]. This aspect of the BMP action together with its osteoinductive power has led to the idea to use the BMPs in the treatment of patients for the enhancement of fracture healing and the augmentation of bone. Initial studies performed with native BMP preparations from human bones [Johnson, E. E. et al., Clin. Orthop. 250 (1990) 234–240; Clin. Orthop. 277 (1992) 229–237] and bovine bones [Sailer, H. F. and Kolb, E., in Bone Morphogenetic Proteins: Biology, Biochemistry and Reconstructive Surgery, pages 207–230, Lindholm, T. S., ed., R. G. Landes Co, 909 Pine St, Georgetown, Tex. 78626, 1996] revealed the efficacy of the BMPs in orthopaedic and cranio-maxillofacial surgery, especially in difficult situations.

Another aspect of the BMPs is their interaction in the manifestation of heterotrophic ossification (HO), which has created expectations to develop inhibitors of the BMPs and use them as therapeutic agents in HO. HO is a frequent complication in patients who have suffered head and neck traumas, traumatic acetabular fracture, or undergone total hip replacement. It is a process of bone formation at ectopic sites, such as muscle and connective tissue, that can lead to decreased mobility, pain, or even total ankylosis, predominantly in hip and elbow joints [for review see: Nilsson, O. S., Acta Orthop. Scand 69 (1998) 667–674]. As the elderly population increases and the number of the total hip arthoplastic operations rises, the number of patients suffering from HO can be expected to grow. Additionally, HO is manifested in some inherited diseases, such as fibrodysplasia, or acquired bone forming lesions, such as spinal hyperostosis, myelopathy and spondylitis ankylosans, in which no curable treatment is available or a surgical operation is the only means of treatment.

Unfortunately, up to now, the discovery of the BMPs has had no impact on the medical treatment of patients, despite encouraging initial results. This is mainly because sufficient amounts of the BMPs or their inhibitors are not available. The purification of the BMPs from natural sources does not result in sufficient amounts of the proteins for treatment purposes, nor are the yields of recombinant human BMPs (rhBMPs) produced in mammalian expression systems satisfactory. Furthermore, individual rhBMPs are not as effective as native human BMP preparations: it has been shown that the latter are ten times more effective in the induction of ectopic bone formation than pure human recombinant BMPs [Bessho, K., et al., Br. J. Oral. Maxillofac. Surg. 37 (1999) 2–5]. Finally, a major problem for a routine application of the BMPs in patients is the lack of a suitable BMP delivery system. The BMPs must be administered with a carrier, since their administration for instance by an injection results in an instant onset of the BMP degradation. This is strikingly contradictory to the BMP expression profiles which show that during fracture healing for instance BMP-2 is expressed up to 14 days after the fracture occurred [Kitazawa, R. et al., Acta Histochem. Cytochem. 31 (1998) 231–236].

Obviously there exists an urgent need for new approaches in the utilization of the BMPs. The present invention provides a solution to overcome the disadvantages and drawbacks described above.

A purpose of the present invention is to provide means for the utilization of the bone forming inductive activity of the BMPs in the treatment of patients in orthopaedics, dentistry and other fields in medicine.

Another purpose of the invention is to provide means for the utilization of the bone forming inhibitory activity of the BMPs in the treatment of patients in orthopaedics and other fields in medicine.

Specifically, a purpose of the present invention is to provide a pharmaceutical composition that would be useful in the treatment of diseases in which the enhancement of fracture healing and the augmentation of bone is desired. Such a composition would improve the recovery of a patient who, e.g., has undergone a surgical bone operation or suffers from accidental bone fracture. In addition, such a composition would find use in the integration of dental implants, in the filling of tooth sockets following extraction, in the alveolar ridge augmentation, in the sinus floor elevation, and in the healing of non-unions.

Additionally, another special purpose of the present invention is to provide a pharmaceutical composition that would be useful in the treatment and prevention of heterotrophic ossification and other diseases involving undesired bone formation. Such a composition would significantly add to the options that now are available in the treatment of HO, and would lack the side effects of the non-steroidal anti-inflammatory drugs (NSAIDs) and the radiotherapy, which at present are the alternative methods of treatment.

Still another purpose of the invention is to provide new methods for the treatment of orthopaedic patients, which would lead to an accelerated and permanent recovery.

Still another purpose of the invention is to provide new methods for the treatment of dental patients, which would lead to an improved dental health.

SHORT DESCRIPTION OF THE INVENTION

Surprisingly it has now been discovered that when stable folding variants of the individual rBMPs or the rBMP monomers, or mutants of either, such as those described in WO 00/56879, are combined, such a combination has a synergistic effect that could not have been expected on the basis of separate properties of the rBMPs or rBMP monomers.

The present invention relates to pharmaceutical compositions containing a mixture of stable folding variants of at least two recombinant bone morphogenetic proteins (rBMPs) or rBMP monomers or mutants of either in a suitable pharmaceutical carrier system.

In a preferred embodiment, the present invention relates to pharmaceutical compositions containing a mixture of stable folding variants of rBMP-2 and rBMP-4 or of their monomers, or mutants of either; a mixture of stable folding variants of rBMP-2 and rBMP-7 or of their monomers, or mutants of either; or a mixture of stable folding variants of rBMP-4 and rBMP-7 or of their monomers, or mutants of either, in a suitable pharmaceutical carrier system.

In another preferred embodiment, the present invention relates to pharmaceutical compositions containing a mixture of stable folding variants of rBMP-2, rBMP-4, and rBMP-7 or of their monomers, or mutants of each, in a suitable pharmaceutical carrier system.

The present invention further relates to the use of the above compositions as inhibitory or inductive agents in therapy, as appropriate.

In a preferred embodiment, the present invention relates to the use of the above compositions as inhibitory or inductive agents, as appropriate, in the treatment of orthopaedic patients.

In another preferred embodiment, the present invention relates to the use of the above compositions as inductive agents in the treatment of dental patients.

In yet another preferred embodiment, the present invention relates to the use of the above compositions as inductive agents in cranio maxillofacial surgery.

The present invention further relates to a method of treatment of orthopaedic patients by administering a therapeutic or prophylactic amount of the above compositions to a patient in the need thereof to either induce or inhibit bone formation, as appropriate.

The present invention still further relates to a method of treatment of dental patients by administering a therapeutic or prophylactic amount of the above compositions to a patient in the need thereof to induce bone formation, as appropriate.

DRAWINGS

The patent or application file contains at least one drawing executed in color. Copies of this patent or patent application publication with color drawing will be provided by the Office upon request and payment of the necessary fee.

Figure 5:
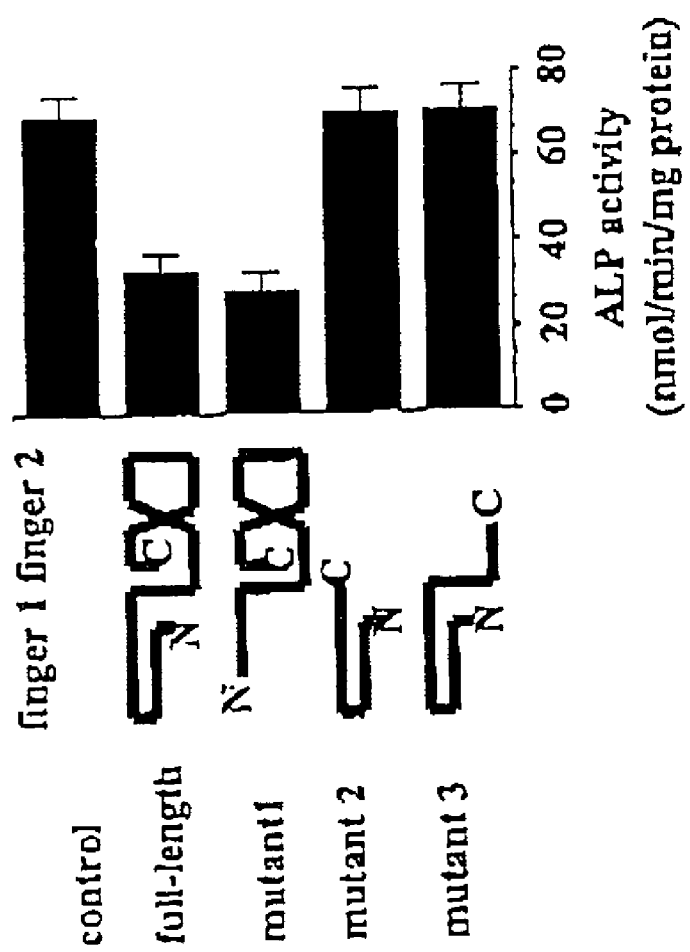

FIG. 5 illustrates the site of inhibition by a mixture of inh-rBMP-2 and inh-rBMP-4 in MC3T3-E1 cells and three truncated mutants of inh-rBMP-4. The left panel shows a schematic view of the structure of the proteins is shown. The right panel shows the corresponding alkaline phosphatase activity of MC3T3-E1 cells treated with the protein. The N- and C-terminus of the proteins are indicated.

DETAILED DESCRIPTION OF THE INVENTION

The present invention is based on the idea to prepare and use a mixture of stable folding variants of rBMP or of rBMP monomers in order to improve the biological action thereof especially in the inhibition of heterotrophic ossification and in the induction of bone formation. Surprisingly it was found that such compositions have synergetic effects, which can be utilized both in an inhibitory manner, i.e. to inhibit development of HO, or in an inductive manner, i.e. to induce formation of new bone. This affords advantages in terms of smaller amounts of the material needed for the desired effect, which is of great importance in view of the laborious production of the rBMPs. Also, a risk of side effects decreases significantly, when smaller amounts can be used.

For the present purposes, the term stable folding variant refers to any stable conformation of the rBMPs or of the rBMP monomers or mutants of either wherein the folding state of the molecule differs in 3-dimentional confirmation from that of the respective mature rBMPs or the rBMP monomers, or wherein the respective mature folding of the rBMPs or the rBMP monomers is obtained via refolding of such a folding state.

For the present purposes, the term rBMP refers to a member of the BMP family as a dimeric recombinant product, and the term rBMP monomer refers to a mature gene expression product, which is either capable of dimerization to form a rBMP dimer or which is not capable of dimerization due to folding. Accordingly, the term rBMP covers the members of the BMP subfamily, such as BMP-2 and BMP-4, the members of the OP subfamily, such as OP-1 (or BMP-7) OP-2 (or BMP-8), BMP-5, BMP-6 (or Vgr-1), the members of the CDMP subfamily, such as CDMP-1 (or BMP-14 or GDF-5), the members of the GDF subfamily, such as GDF-1, GDF-3, GDF-8, GDF-9, GDF-11 (or BMP-11), GDF-12 and GDF-14, and the members of other BMP subfamilies, such as BMP-3 (or osteogenin), BMP-9 (or GDF-2), and BMP10, when produced by recombinant technology. The rBMPs or the rBMP monomers useful in the composition of the present invention include especially the folding variants of rBMP-2, rBMP-4 and rBMP-7 or monomers thereof, which at present are known to be critically involved in the formation of new bone. However, the scope of the invention is also intended to cover compositions containing the folding variants of those rBMPs or monomers thereof, whose role in the bone formation has not so far been clarified.

For the present purposes, the term inductive refers to the capacity of the composition or individual stable folding variants of the rBMPs to induce the formation of new bone.

For the present purposes, the term inhibiting refers to the capacity of the composition or individual stable folding variants of the rBMP monomers to prevent the formation of new bone.

The stable folding variants of the rBMP or the rBMP monomers or mutants of either useful in the present invention can be prepared by standard recombinant technology using both prokaryotic and eukaryotic expression systems in a conventional manner. In this respect, a reference is made for instance to Cerletti et al. (European Patent Application 0 433 225 A1) and Israel D. I. et al., Growth Factors 7 (1992) 139–150. The production in a prokaryotic expression system, such as in *Eschericia coli* strains or in other suitable bacterial strains, offers advantages in terms of the yield. Prokaryotic expression systems are especially suitable for the production of the rBMP monomers. On the other hand, eukaryotic expression systems, such as mammalian or insect cells, especially mammalian cells and especially those using a protein-free medium, are advantageous in terms of the product safety. Examples of suitable mammalian cells include Chinese hamster ovarian cells (CHO). Mammalian expression systems are especially suitable for the production of the rBMP dimers. The choice of a suitable production system is well within the knowledge of a man skilled in the art. The stable folding variants of the rBMP and the rBMP monomers useful in the present invention are further treated, where necessary, by subjecting the respective rBMPs or the rBMP monomers to such conditions that amend, optionally reversibly, the capability of dimerization of said rBMP or the rBMP monomers. Such conditions include a treatment with a chaotropic agent in a suitable buffer for a period of time sufficient to amend the stereochemistry of the monomers so that dimerization does not occur. As suitable chaotropic agents urea, guanidine hydrochloride, imidozole, and thiosulphate at a concentration of at least 3 M, preferably 3–8 M, and most preferably 5–8 M, can be mentioned. Preferably urea at a concentration of 5–8 M and most preferably at a concentration of 6 M, is used. Another preferred chaotrop is guanidine hydrochloride at a concentration of 3–6 M, preferably at a concentration of 6 M.

Instead of a chaotropic agent a suitable reducing agent can be used. Suitable reducing agents include dithiotreitol at a concentration of 0.05–1 mM, preferably 0.1 mM, and mercaptoethanol at a concentration of 0.1–10 mM, preferably 1 mM.

Also a treatment with a suitable oxidazing agent can be used. In this respect a reference is made for example to European Patent Application 0 433 225 A1 and U.S. Pat. No. 5,756,308. Other conditions, such as temperature, pH, ionic strength and like can be used to create stable folding variants of the rBMPs or to assist the function of the above agents.

Alternatively, the stable folding variants useful in the invention are mutant forms of respective rBMPs or the rBMP monomers, which are obtainable for instance by a deletion of an amino acid or amino acids from the polypeptide sequence of a rBMP or a rBMP monomer, by an insertion of an additional amino acid or amino acids to the polypeptide sequence of a rBMP or a rBMP monomer. These procedures are well known to the persons skilled in the art and include a treatment with a suitable protease or a use of recombinant technology.

The period of time sufficient for a successful treatment depends on the agent used, but it is usually is at least 10–100 hours, preferably 10–50 hours, and most preferably 24 hours. Similarly, the temperature employed varies with the respective agent, but temperatures at the range of 3–24° C., preferably 4° C. can be employed.

Buffers useful in the production include phosphate buffers with or without saline, Tris-buffers and like having a pH of 6 to 8, preferably 8, and a concentration of 5–100 mM. A 20 mM Tris buffer, pH 8, is especially suitable.

The stable folding variants of the rBMP and the BMP monomers useful in the present invention are purified in a conventional manner, such as by chromatographic methods, preferably by gel filtration and/or affinity chromatography, by dialysis, by membrane filtration and like. These methods are well known to persons skilled in the art.

The stable folding variants of the rBMPs thus prepared are initially in a form of monomers, and for the inhibitory aspect of the invention, the composition of the invention preferably contains the respective stable folding variants of the rBMPs as monomers. However, an rBMP dimer having one of the monomers or both monomers suitably treated to prevent the natural folding is equally suitable for inhibitory purposes of the invention. For inductive purposes, the rBMP monomers are allowed to dimerisize spontaneously or such a dimerization can be facilitated by the choice of, e.g., the buffer.

Figure 3:
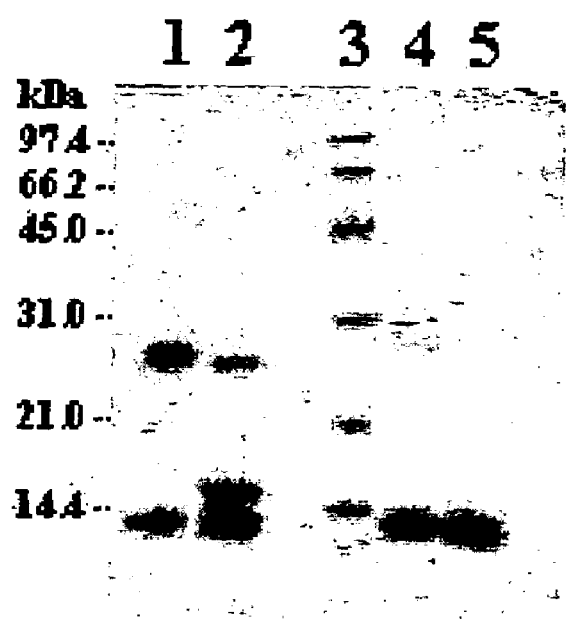
FIG. 3 shows the separation of mature rBMP-2 folding variants by SDS PAGE: (1) inh-rBMP-2 isolated from *E. coli*; (4) inh-rBMP-2 isolated from *E. coli* in reduced form; (2) ind-rBMP-2 after in vitro refolding; (5) ind-rBMP after in vitro refolding; (3) molecular weight markers.

The inhibitory (inh) and inductive (ind) folding variants of each respective rBMP and rBMP monomers useful in the present invention have identical amino acid sequences but they differ in respect of disulfide bond formation and consequently of the 3-dimentional structure. For instance, the folding variants inh-rBMP-2 and ind-rBMP-2 have a sufficiently different mobility so that they can be distinguished by SDS PAGE (FIG. 3). Due to the instant degradation of the rBMPs or the rBMP monomers upon contact with body fluids and due to their strong morphogenetic action, topical administration routes are preferred. This makes the choice of the carrier system critical. Thus, suitable carriers for the composition of the invention are solid or semisolid biodegradable carriers, which can be implanted in the patient. Such systems include those based on collagen, fibrin, hydrogels, hydroxyapatite (HA), such as HA-fibrin composite, HA-collagen composite, HA-calcium sulphate, or biogradable polymers, such polyanhydrides, poly(lactic acid)s (PLA), poly(lactide-co-glycolide)-poly(ethyleneglycol) (PLG-PEG) copolymers, PLG-PGA copolymers and like. Biodegradable polymers are preferred.

In a preferred embodiment, the composition of the invention contains a carrier, which is a slow release system based on biogradable polymers, such as hydrogels, or in particular polyesters, for instance polyglycolide (PGA), polylactide (PLA) and like polymers, or copolymers thereof, such as copolymers of polylactide with glycolides, ε-caprolactine, δ-valerolactone or 1,5-dioxepan-2-one. Preferably, the copolymers of polylactide with glycolides, such as poly-DL-lactide-co-glycolide (PLGA), are used as a carrier.

The compositions of the invention may contain, for example, 0.1–2 mg of the stable folding variants of the rBMPs or rBMP monomers. However, the amount of the folding variant varies in different applications. Thus, smaller amounts may be sufficient in some applications whereas somewhat larger amounts may be needed for the desired effect in other applications.

The dosage of the compositions of the invention depends on the individual patients and the disorder to be treated. An exemplary single dose of the composition of the invention is within the range of 0.1–2 mg. However, a smaller dose may be sufficient in some disorders whereas somewhat larger doses may be needed for the desired effect in other treatments.

The compositions of the invention contain stable folding variants of at least two rBMPs or the BMP monomers or mutants of either in a weigh ratio of 1–10:1–10, preferably in a weight ratio 1–5:1–5. In the most preferred embodiment the weight ratio of stable folding variants is 1:1. When more than two rBMPs or the BMP monomers or mutants of either are used, the weight ratio of stable folding variants is at the range of 1–10:1–10:1–10, preferably at the range of 1–5:1–5:1–5, the weight ratio of 1:1:1 being most preferred.

Figure 1:
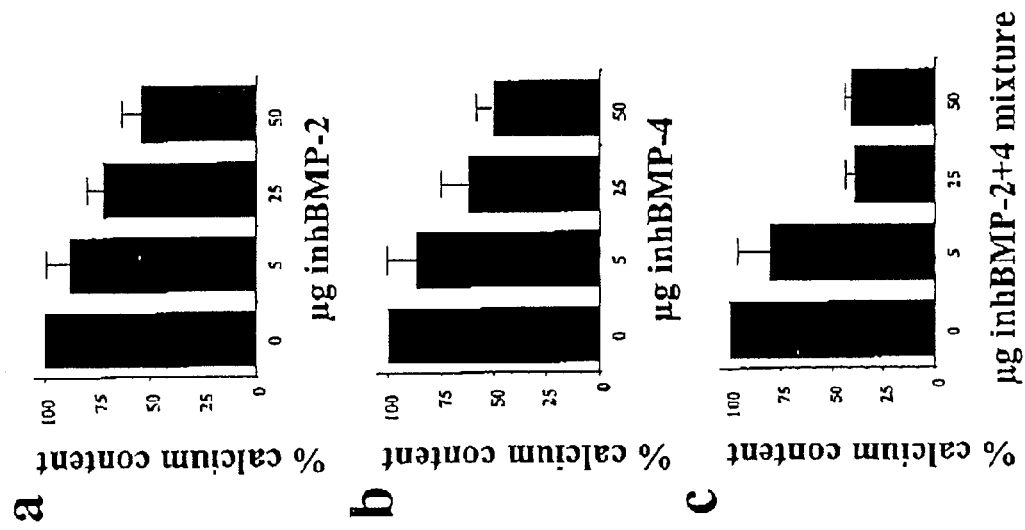
FIG. 1 shows the inhibition of ossification in demineralized bone containing inh-rBMP monomers: a) inh-rBMP-2; b) inh-rBMP-4; and c) inh-rBMP-2 plus inh-rBMP-4.

The present invention provides for the first time means for the utilization of bone morphogenetic proteins in the treatment of patients suffering from diseases or disorders involving undesired bone formation, such as heterotrophic ossification. Additionally, the present invention provides means for the augmentation of the formation of new bone in the treatment of bone fractures and other injuries. The compositions of the present invention allow the use of the rBMPs and the rBMP monomers to achieve the desired effect in significantly smaller amounts than corresponding individual polypeptides. Thus, when inh-rBMP-2 and inh-rBMP-4 monomers were applied as 1:1 mixture, a dose as low as 25 μg was sufficient to reduce the calcium content to 39% of the control value, whereas with the individual rBMPs when applied individually the reduction percent of 50% or more was obtained with a dose of 50 μg (FIG. 1).

The invention is illustrated by the following examples, which are given only for illustrative purposes.

For statistical analysis, Student's T-test was implemented by a commercially available software package (SSPE, Chicago, ll). All values are represented as means ± standard error of the mean.

EXAMPLE 1

Expression, Purification, and Refolding of Bacterial Derived Inhibitory Recombinant Bone Morphogenetic Proteins (inh-rBMPs)

In a first step, the human placenta library (Clontech, Palo Alto, Calif.) was used as a template for the isolation of full-length cDNAs for human BMP-2 and human BMP-4 using the polymerase chain reaction (PCR). A 500 bp long 5-prime end of each PCR derived clone was subsequently used to screen the lambda gt10 library by colony hybridisation, in order to isolate a non-amplified cDNA clone. Both strands of the final full-length clones were sequenced by the dideoxynucleotide-chain-termination method using the Sequenase 2.0 kit (USB, Cleveland, Ohio). The nucleotides were read with a digitised gel reader and analysed with the software package GCG (University of Wisconsin Genetics Computer Group).

For the expression of inhibitory bone morphogenetic proteins inh-rBMP-2 and inh-rBMP-4, mature rBMP expression constructs were generated by PCR with the respective full-length clones as template. The initial ATG placed in front of the mature rBMP-2 sequence (sequence id. No. 1) and rBMP-4 sequence (sequence id. No. 2) was mutagenized into the construct by the introduction of an Nde-restriction site. This allowed cloning into the pET23b+ expression vector [Studier et al., Methods Enzymol 185 (1990) 60–89] used for the transformation of *Escherichia coli* strain BL21 (DE3). The cells were grown to an optical density of 0.6 (at 600 nm), induced by the addition of isopropyl 13-D-thiogalactopyranoside to a final concentration of 0.4 mM, and harvested 3 h after induction by centrifugation at 5,000× g. The pellet was stored overnight at −80° C. After thawing the cells were resuspended in 20 mM Tris-HCl, pH 7.9, 0.5 M NaCl, 5 mM imidazole, and lysed by three passages through a French pressure cell at 20,000 psi. After centrifugation, rBMPs monomers were present in the pellet. To produce inh-rBMP, the pellet was dissolved in the same buffer as before with the addition of 6 M urea and incubated on a turning wheel for seven days at 4° C. Insoluble material was removed by centrifugation at 15,000× g for 30 min, and the supernatant dialyzed extensively against 10 mM Tris-HCl, pH 8, 6 M urea (TU), applied to an affinity column (heparin, 5 ml HiTrap®, Pharmacia Biotech), and eluted with 2 M NaCl in TU. Inh-rBMP monomers and dimers were separated by gel filtration (HiLoad® Superdex®) 200, Pharmacia Biotech, 1.6 cm×60 cm; 124 ml). The purity of inh-rBMP monomers and dimers was analyzed by Coomassie stained SDS PAGE and exceeded 99% (FIG. 3).

As can be seen in FIG. 3, the material consists of a dimeric fraction as well as monomers that were identified as inh-rBMP-2 and inh-rBMP-4. Close inspection of the SDS PAGE gels reveals that the broad band corresponding to the dimeric fraction consists of at least three distinguishable proteins, indicating the presence of three conformers of the same protein.

EXAMPLE 2

Production of rhBMP-4 in Chinese Hamster Ovary Cells Using a Protein Free Cell Culture Medium Full-length cDNA for rhBMP-4 (sequence id. No 3) was cloned into the pMPSV-HE vector (gift of Prof. Hauser, Braunschweig, Germany), which carries the promoter for myeloproliferative sarcoma virus 1 and cotransfected in a ratio of 50:1 with pMSVtrp 33 into Chinese hamster ovary cells (Cytos Biotechnology GmbH and Dr Messi, Cell Culture Technologies, Zurich, Switzerland). The plasmid pMSVtrp contains the tryptophan synthase (trpB) gene of *E. coli* and allows the cells to survive in medium where tryptophan is substituted by indole. Transfections were performed in 6-well plates with FUGENE® (Roche Basel) following the manufactures recommendations. A day after transfection an equal amount of medium containing indole instead of tryptophan was added. Three days after transfection cells from one well were diluted 1:30 in medium with indole and seeded into 48 wells of 12-well plates. Individual clones recognizable after two weeks were tested for rhBMP-4 production by immunoblot analysis using an anti-BMP-4 polyclonal antibody raised in rabbits.

For large scale production, the cells were grown in one liter spinner flasks in FMX-8 medium (Dr Messi, Cell Culture Technologies, Zurich, Switzerland) at 37°, 5% $CO_2$, 40 rpm, and rotation of 720°. After five days the cells were removed by centrifugation, the supernatant applied to a HiTrap® heparin column, and rhBMP-4 eluted by 2 M NaCl in TU. Further purification steps involved gel filtration (HiLoad® Superdex® 75 column, Pharmacia Biotech, 1.6 cm×60 cm; 124 ml), ion-exchange chromatography (Mono Q, 1 ml, FPLC, Pharmacia), and the similar reversed phase column used for the purification of bacterial derived rBMP monomers.

The above procedure can be applied for the production of other rBMPs monomers in a eukaryotic system. The amendments required are well within the knowledge of persons skilled in the art.

EXAMPLE 3

Inhibition of Heterotopic Ossification Induced by Demineralized Bone

To determine the synergetic effect of inh-rBMP monomers 2 and 4 (see Example 1) on ossification, demineralized bone powder was prepared from rat long bones essentially as described by Muthukumaran, N. et al., Collagen Rel. Res. 8 (1988) 433–441. To produce inactivated bone collagen, demineralized bone material was extracted with 4 M guanidine hydrochloride [Sampath, T. K. and Reddi, A. H., Proc. Natl. Acad. Sci. USA 78 (1981) 7599–7603]. For loading, 25 mg of the demineralized material was weighted into a microcentrifuge tube and 120 µl of inh-rBMPs of Example 1 in 0.05 mM HCl containing 0.5 mg of chondroitin sulfate were added. The control was prepared accordingly without the protein. After incubation at room temperature for one hour, 0.3 ml of rat-tail collagen (2 mg/ml in 0.1% acetic acid) was added to the carrier material, mixed by vortexing and then incubated for another 30 min. The loaded material was then mixed with 1.1 ml of EtOH (stored at –80° C.) and transferred to a –80° C. freezer for 1 h. The suspension was centrifuged for 30 min at 4° C., the supernatant removed and the pellet washed three times with 85% EtOH (–20° C.). The final pellet was formed in a 1 ml syringe and dried under a sterile hood over night.

Dried pellets were implanted subcutaneously in the thoracic region of anaethetized Sprague-Dawley rats weighing between 200 and 300 g and one pellet was implanted on each side of the thorax.

Demineralized bone preparations containing inh-rBMPs were placed subcutaneously over both sides of the thorax of the rats. In each animal, one implant was treated with 5 µg, 25 µg or 50 µg of the rBMP monomers and the opposite implant untreated. After 21 days the implants were removed and the extent of ossification was determined by the measurement of their calcium content. A fraction of the implant was weighed and homogenized with an omni-mixer (Waterbury, Conn., USA) in 1.5 ml of 3 mM $NaHCO_3$, 150 mM NaCl. After centrifugation (1000× g 15 min), the pellet was resuspended three times with 1 ml of 10 mM Tris-HCl, pH 7, and mixed at room temperature for 1 h. After the final wash, the pellets were extracted overnight with 1 ml 0.5 M HCl. The calcium content in the extract was measured by atomic absorption spectroscopy.

The results are shown in FIGS. 1a and 1b. As can be seen therefrom, both inh-rBMP-2 and inh-rBMP-4 monomers, which are 87% identical at the amino acid level, are capable of reducing the calcium content of the implants in a dose-dependent manner. However, when inhBMP-2 and inh-BMP-4 monomers are applied as 1:1 mixture, a dose as low as 25 µg is sufficient to reduce the calcium content to 39% of the control value (FIG. 1c).

Additionally, most of the implants were examined histologically to assess the influence of inh-rBMP monomers at the cellular level. The implants were fixed and then embedded in poly(methyl-methacrylate). Histological sections 4.5 µm thick were prepared and stained with Goldner-Trichrome and toluidine blue stains. The stained sections were examined for bone formation, cell type, morphology, and stromal details using bright-field light microscopy.

Figure 2:
FIG. 2 shows the histological effect of inh-rBMP-2 monomers after 21 days: a) unloaded implant; b) inh-rBMP-2 loaded implant; c) inh-rBMP-2 loaded implant a 5× higher magnification.

No sign of any inflammatory immune reaction or other abnormality can be detected. The only obvious response to a single inh-rBMP monomer dose is a retardation of the ossification of the implant (FIG. 2).

EXAMPLE 4

Inhibitory Effect of inh-rBMSs at the Cellular Level

The murine osteoblastic cell line MC3T3-E1 was used to study inhibitory effects of inh-rBMP-2 and inh-rBMP-4 at the cellular level. These cells produce endogenous BMP-2 and BMP-4 and differentiate autocrine into mature osteoblasts under their influence [Natsume, T., et al., J. Biol. Chem. 272 (1997) 11535–11540]. This process can be monitored by the increase in alkaline phosphatase (AP) activity.

MC3T3-E1 cells were grown in an alpha-modified Minimum Essential Medium (Life Technologies, Inc., Grand Island, N.Y. USA) containing 10% fetal calf serum (Life Technologies, Inc.), 50 µg/ml gentamycin, and 50 µg/ml ascorbic acid. To examine the biological activity of rBMP folding variants, $1\times10^5$ cells per well were plated in 6-well plates and the protein added subsequently. Medium exchange was performed after 3 days and alkaline phosphatase was determined on day 6. The cells were washed 3 times with phosphate buffered saline, and the cells from a single well were combined in 0.5 ml of lysis buffer (0.56 M 2-amino-2-methyl-propane-1-ol, pH 10) and homogenized by an omni-mixer. 200 µl of the cell lysate were mixed with 200 µl of lysis buffer supplemented with 20 mM p-nitrophenylphosphate and 4 mM MgC12 at 4° C.

Alkaline phosphatase activity was determined according to Lowry, O. et al. [J. Biol. Chem. 207 (1954) 19–37]. p-nitrophenol liberated was converted to p-nitrophenylate by adding 400 µl of 1 M NaOH, which was quantitated by measuring the absorbance at 410 nm (epsilon=17500/molxcm). Alkaline phosphatase activity was normalized to total protein and expressed as nmol nitrophenylate generated per min per mg protein.

Figure 4:
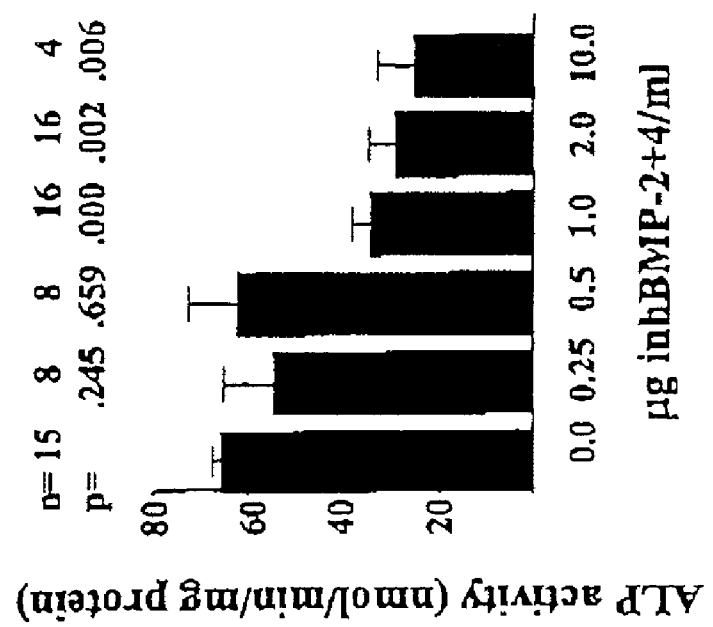
FIG. 4 shows the alkaline phosphatase activity determined in MC3T3-E1 cells under the influence of a 1:1 mixture of inh-rBMP-2 and inh-rBMP-4.

Treatment of MC3T3-E1 cells with monomeric inh-rBMP-2 or inh-rBMP-4 alone does not produce significant reduction of AP activity. However, when applied as 1:1 mixture, inh-rBMP-2 and inh-rBMP-4 monomers reduce AP activity in a dose-dependent manner (FIG. 4).

EXAMPLE 5

Structural Elements and Site of Inhibition Within inh-rBMPs

To investigate which structural elements within inh-rBMP-4 are involved in inhibition, MC3T3-E1 cells were used. A 1:1 mixture of mature inh-rBMP-4 and inh-rBMP-2 and three deletion mutants of inh-rBMP-4. Mature BMP expression constructs were generated by PCR with the respective cDNAs as templates. A start codon as part of a Nde-restriction site was introduced by a PCR reaction [Weber, F. et al., *Cell Mol Life Sci* 54 (1998) 751–759] in front of the mature BMP sequence [Wozney, J. M. et al., Prog Growth Factor Res 1 (1989) 267–280], which added a N-terminal extension of a single methionine to the mature sequence. The deletion mutants were created accordingly by the insertion of a stop codon in mutant 1 and 2 or the insertion of a start codon at defined positions, using procedures known to persons skilled in the art.

MC3T3-E1 cells were treated with 1 μg protein/ml of a 1:1 mixture of mature inh-rBMP-4 and inh-rBMP-2 or with 1 μg protein/ml from the inh-rBMP-4 mutants and their alkaline phosphatase activity was analyzed.

The amino acid sequence of mature BMP-4, which is identical to inh-rBMP-4 contains 115 amino acids. Mutant 1 spans amino acids 46 to 115; mutant 2 amino acids 1 to 55 and mutant 3 amino acids 1 to 88. The cysteine responsible for dimerisation is located at position 79 and is therefore present in mutants 1 and 3. The cysteine residues involved in the formation of the cysteine-knot are at positions 14, 43, 47, 79, 111 and 113 and accordingly, none of the mutants was capable of forming the entire cysteine-knot structure.

Mutant 1 of inh-rBMP-4, covers the entire region involved in the formation of finger 2, but not that of finger 1. Mutants 2 and 3 contain only the region for finger 1, but not of finger 2. As shown in FIG. 5, mutant 1, but not mutants 2 or 3, was able to reduce AP activity in MC3T3E1 cells, while the presence or absence of cysteine 79, which is involved in dimer formation, did not correlate with the cellular response. Thus, the amino acid sequence responsible for the inhibition of ossification resides in the C-terminal half of mature BMP, the region where an anti parallel B-sheet, adopting a twisted crossover conformation, forms finger 2.

The invention claimed is:

1. A method of inhibiting bone formation comprising administering to a patient a therapeutic or prophylactic amount of a composition containing a synergistic mixture of at least two recombinant bone morphogenetic protein monomers in a suitable pharmaceutical carrier system, wherein the at least two rBMP monomers are selected from the group consisting of rBMP-2, encoded by SEQ ID NO:1 and rBMP-4, encoded by SEQ ID NO:2, wherein the at least two rBMP monomers provide a synergistic therapeutic or prophylactic effect, and wherein the synergistic mixture of at least two rBMP monomers is generated by contacting said at least two rBMP monomers with urea for a period of time sufficient to prevent dimerization of said at least two rBMP monomers.

2. A method of claim 1, wherein administering said composition comprises treating an orthopedic patient.

3. A method of claim 2, wherein administering said composition comprises treating heterotrophic ossification and other diseases involving undesired bone formation.

4. A method of claim 2, wherein the patient suffers from head trauma, neck trauma, traumatic acetabular fracture, fibrodysplasia, spinal hyperostosis, mvelopathy or spondylitis ankylosans or has undergone hip replacement.

5. A method of claim 1, wherein administering said composition comprises treating a dental patient.

6. A method of claim 1, wherein said composition is administered to a subject having cranio maxillofacial surgery.

7. A method of inhibiting bone formation in orthopedic patients comprising administering a therapeutic or prophylactic amount of a composition containing a synergistic mixture of at least two rBMP or their monomers in a suitable pharmaceutical carrier system to a patient, wherein the at least two rBMP monomers are selected from the group consisting of rBMP-2, encoded by SEQ ID NO:1 and rBMP-4, encoded by a SEQ ID NO:2, wherein the at least two rBMP monomers provide a synergistic therapeutic or prophylactic effect, and wherein the synergistic mixture of at least two rBMP monomers is generated by contacting said at least two rBMP monomers with urea for a period of time sufficient to prevent dimerization of said at least two rBMP monomers.

8. A method of inhibiting bone formation in dental patients comprising administering a therapeutic or prophylactic amount of a composition containing a synergistic mixture of at least two rBMP monomers in a suitable pharmaceutical carrier to a patient, wherein the at least two rBMP monomers are selected from the group consisting of rBMP-2, encoded by SEQ ID NO:1 and rBMP-4, encoded by SEQ ID NO:2, wherein the at least two rBMP monomers provide a synergistic therapeutic or prophylactic effect, and wherein the synergistic mixture of at least two rBMP monomers is generated by contacting said at least two rBMP monomers with urea for a period of time sufficient to prevent dimerization of said at least two rBMP monomers.

9. A method of inhibiting bone formation comprising administering to a patient a therapeutic or prophylactic amount of a composition containing a synergistic mixture of at least two rBMP monomers in a suitable pharmaceutical carrier system, wherein the at least two rBMP monomers are selected from the group consisting of rBMP-2, encoded by a of SEQ ID NO:1 and rBMP-4, encoded by SEQ ID NO:2, wherein the at least two rBMP monomers provide a synergistic therapeutic or prophylactic effect, wherein said at least two rBMP monomers are present in a weight ratio of 1:10 to 10:1, and wherein said synergistic mixture of at least two rBMP monomers is generated by contacting said at least two rBMP monomers with urea for a period of time sufficient to prevent dimerization of said at least two rBMP monomers.

10. A method of claim 9, wherein said urea is present at a concentration of at least 3 M.

11. A method of claim 10, wherein said urea is present at a concentration of between 5 M and 8 M.

12. A method of claim 9, wherein said weight ratio is between 1:5 to 5:1.

13. A method of claim 9, wherein said weight ratio is 1:1.

* * * * *

SEQUENCE LISTING

<160> NUMBER OF SEQ ID NOS: 3

<210> SEQ ID NO 1
<211> LENGTH: 381
<212> TYPE: DNA
<213> ORGANISM: Homo sapiens

<400> SEQUENCE: 1

```
atgcaagcca aacacaaaca gcggaaacgc cttaagtcca gctgtaagag acacccttrg    60
tacgtggact tcagtgacgt ggggtggaat gactggattg tggctccccc ggggtatcac   120
gccttttact gccacggaga atgcccttt cctctggctg atcatctgaa ctccactaat    180
catgccattg ttcagacgtt ggtcaactct gttaactcta agattcctaa ggcatgctgt   240
gtcccgacag aactcagtgc tatctcgatg ctgtaccttg acgagaatga aaaggttgta   300
ttaaagaact atcaggacat ggttgtggag ggttgtgggt gtcgctagta cagcaaaatt   360
aaatacataa atatatatat a                                             381
```

<210> SEQ ID NO 2
<211> LENGTH: 484
<212> TYPE: DNA
<213> ORGANISM: Homo sapiens

<400> SEQUENCE: 2

```
atgagcccta agcatcactc acagcgggcc aggaagaaga ataagaactg ccggcgccac    60
tcgctctatg tggacttcag cgatgtgggc tggaatgact ggattgtggc cccaccaggc   120
taccaggcct tctactgcca tgggactgc ccctttccac tggctgacca cctcaactca    180
accaaccatg ccattgtgca gacctggtc aattctgtca attccagtat ccccaaagcc    240
tgttgtgtgc ccactgaact gagtgccatc tccatgctgt acctggatga gtatgataag   300
gtggtactga aaaattatca ggagatggta gtagagggat gtgggtgccg ctgagatcag   360
gcagtccttg aggatagaca gatatacaca ccacacacac acaccacata caccacacac   420
```

-continued

```
acacgttccc atccactcac ccacacacta cacagactgc ttccttatag ctggactttt    480
attt                                                                484

<210> SEQ ID NO 3
<211> LENGTH: 1751
<212> TYPE: DNA
<213> ORGANISM: Homo sapiens

<400> SEQUENCE: 3
ggcagaggag gagggaggga gggaaggagc gcggagcccg gcccggaagc taggtgagtg     60
tggcatccga gctgagggac gcgagcctga gacgccgctg ctgctccggc tgagtatcta    120
gcttgtctcc ccgatgggat tcccgtccaa gctatctcga gcctgcagcg ccacagtccc    180
cggccctcgc ccaggttcac tgcaaccgtt cagaggtccc caggagctgc tgctggcgag    240
cccgctactg cagggaccta tggagccatt ccgtagtgcc atcccgagca acgcactgct    300
gcagcttccc tgagcctttc cagcaagttt gttcaagatt ggctgtcaag aatcatggac    360
tgttattata tgccttgttt tctgtcaaga caccatgatt cctggtaacc gaatgctgat    420
ggtcgtttta ttatgccaag tcctgctagg aggcgcgagc catgctagtt tgatacctga    480
gacggggaag aaaaaagtcg ccgagattca gggccacgcg ggaggacgcc gctcagggca    540
gagccatgag ctcctgcggg acttcgaggc gacacttctg cagatgtttg ggctgcgccg    600
ccgcccgcag cctagcaaga gtgccgtcat tccggactac atgcgggatc tttaccggct    660
tcagtctggg gaggaggagg aagagcagat ccacagcact ggtcttgagt atcctgagcg    720
cccggccagc cgggccaaca ccgtgaggag cttccaccac gaagaacatc tggagaacat    780
cccagggacc agtgaaaact ctgcttttcg tttcctcttt aacctcagca gcatccctga    840
gaacgaggtg atctcctctg cagagcttcg gctcttccgg gagcaggtgg accagggccc    900
tgattgggaa aggggcttcc accgtataaa catttatgag gttatgaagc ccccagcaga    960
agtggtgcct gggcacctca tcacacgact actggacacg agactggtcc accacaatgt   1020
gacacggtgg gaaacttttg atgtgagccc tgcggtcctt cgctggaccc gggagaagca   1080
gccaaactat gggctagcca ttgaggtgac tcacctccat cagactcgga cccaccaggg   1140
ccagcatgtc aggattagcc gatcgttacc tcaagggagt gggaattggg cccagctccg   1200 gccccctcctg gtcaccttttg gccatgatgg ccggggccat gccttgaccc gacgccggag   1260
ggccaagcgt agccctaagc atcactcaca gcgggccagg aagaagaata agaactgccg   1320
gcgccactcg ctctatgtgg acttcagcga tgtgggctgg aatgactgga ttgtggcccc   1380
accaggctac caggccttct actgccatgg ggactgcccc tttccactgg ctgaccacct   1440
caactcaacc aaccatgcca ttgtgcagac cctggtcaat tctgtcaatt ccagtatccc   1500
caaagcctgt tgtgtgccca ctgaactgag tgccatctcc atgctgtacc tggatgagta   1560
tgataaggtg gtactgaaaa attatcagga gatggtagta gagggatgtg ggtgccgctg   1620
agatcaggca gtccttgagg atagacagat atacacacca cacacacaca ccacatacac   1680
cacacacaca cgttcccatc cactcaccca cacactacac agactgcttc cttatagctg   1740
gacttttatt t                                                       1751
```